United States Patent
Tsai

(10) Patent No.: US 9,723,974 B2
(45) Date of Patent: Aug. 8, 2017

(54) IMAGE TYPE LARYNGOSCOPE APPARATUS

(71) Applicant: Yung-Hsuan Tsai, Kaohsiung (TW)

(72) Inventor: Yung-Hsuan Tsai, Kaohsiung (TW)

(*) Notice: Subject to any disclaimer, the term of this patent is extended or adjusted under 35 U.S.C. 154(b) by 417 days.

(21) Appl. No.: 14/585,230

(22) Filed: Dec. 30, 2014

(65) Prior Publication Data

US 2016/0183766 A1 Jun. 30, 2016

(51) Int. Cl.
- *A61B 1/00* (2006.01)
- *A61B 1/267* (2006.01)
- *A61B 13/00* (2006.01)
- *A61B 1/04* (2006.01)

(52) U.S. Cl.
CPC ........ *A61B 1/0014* (2013.01); *A61B 1/00016* (2013.01); *A61B 1/00052* (2013.01); *A61B 1/00105* (2013.01); *A61B 1/00165* (2013.01); *A61B 1/042* (2013.01); *A61B 1/267* (2013.01); *A61B 13/00* (2013.01)

(58) Field of Classification Search
CPC .............................. A61B 1/0014; A61B 1/267
See application file for complete search history.

(56) References Cited

U.S. PATENT DOCUMENTS

| | | | | |
|---|---|---|---|---|
| 5,897,489 A | * | 4/1999 | Urbanowicz | A61B 1/0014 600/185 |
| 6,083,151 A | * | 7/2000 | Renner | A61B 1/00135 600/112 |
| 8,398,545 B2 | * | 3/2013 | Chen | A61B 1/267 600/188 |
| 8,715,172 B1 | * | 5/2014 | Girgis | A61B 1/267 600/188 |
| 2011/0099773 A1 | * | 5/2011 | Golden | A61B 1/0014 24/457 |
| 2014/0223701 A1 | * | 8/2014 | Bean | A61B 1/00133 24/483 |
| 2015/0112146 A1 | * | 4/2015 | Donaldson | A61B 1/00048 600/188 |
| 2016/0051781 A1 | * | 2/2016 | Isaacs | A61M 16/0488 600/188 |

* cited by examiner

*Primary Examiner* — David Bates
*Assistant Examiner* — Olivia C Chang
(74) *Attorney, Agent, or Firm* — Alan D. Kamrath; Kamrath IP Lawfirm, P.A.

(57) ABSTRACT

An image type laryngoscope apparatus includes a laryngoscope (3), a fastening device (1) and an image device (2). The image device is attached to the laryngoscope by the fastening device, and the signal transmitting unit (21) of the image device transmits image signals to a monitor (24) in a wire transmission manner or to a mobile device (4) in a wireless transmission manner, so that the operator can clearly inspect the present condition of a patient's throat by the image signals.

7 Claims, 6 Drawing Sheets

IMAGE TYPE LARYNGOSCOPE APPARATUS

BACKGROUND OF THE INVENTION

1. Field of the Invention

The present invention relates to a medical tool for aid of intubation or cannulation and, more particularly, to an image type laryngoscope apparatus.

2. Description of the Related Art

A conventional laryngoscope apparatus comprises a laryngoscope, an image capture device and an image display panel. Thus, the operator can inspect the present condition of a patient's throat by use of the laryngoscope apparatus to facilitate the intubation (or cannulation) process. However, the parts of the laryngoscope apparatus are formed integrally so that it is necessary throw away the whole laryngoscope apparatus when one of the parts are worn out or fail, thereby causing a waste of the laryngoscope apparatus. In addition, when the laryngoscope apparatus is replaced by a new one, the operator has to learn new operational methods and skills and has to change his/her operational customs or habits, thereby limiting the versatility of the laryngoscope apparatus.

BRIEF SUMMARY OF THE INVENTION

In accordance with the present invention, there is provided an image type laryngoscope apparatus comprising a laryngoscope, a fastening device and an image device. The laryngoscope includes a handle and a tongue pressing plate connected with the handle. The fastening device includes two clamping members, a connecting rod and a driving lever. Each of the clamping members is provided with an arcuate groove abutting the handle of the laryngoscope. Each of the clamping members has a first end and a second end. The first end of each of the clamping members is provided with a pivot end, and the pivot ends of the clamping members are pivotally connected with each other. The second end of one of the clamping members is provided with an elongate slot. The connecting rod is inserted into the elongate slot. The connecting rod has a first end pivotally connected with the second end of the other one of the clamping members. The driving lever is pivotally connected with a second end of the connecting rod. The image device includes a signal transmitting unit, a guide pipe, a camera lens and a monitor. The signal transmitting unit is mounted on one of the clamping members. The guide pipe is connected with the signal transmitting unit. The camera lens is mounted on a front end of the guide pipe and is located at a front end of the tongue pressing plate of the laryngoscope. The monitor is connected with the signal transmitting unit by a connecting unit in a wire manner.

According to the primary advantage of the present invention, the image device is attached to the laryngoscope by the fastening device, and the signal transmitting unit transmits the image signals to the monitor in a wire transmission manner or to the mobile device in a wireless transmission manner, so that the operator can clearly inspect the present condition of a patient's throat by the image signals.

According to another advantage of the present invention, the image device is attached to the laryngoscope which has a conventional structure so that the operator can operate the laryngoscope instantly without having to change his/her operational customs or habits, and without having to learn new operational methods and skills, thereby facilitating the operator operating the laryngoscope 3, and thereby saving the cost.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
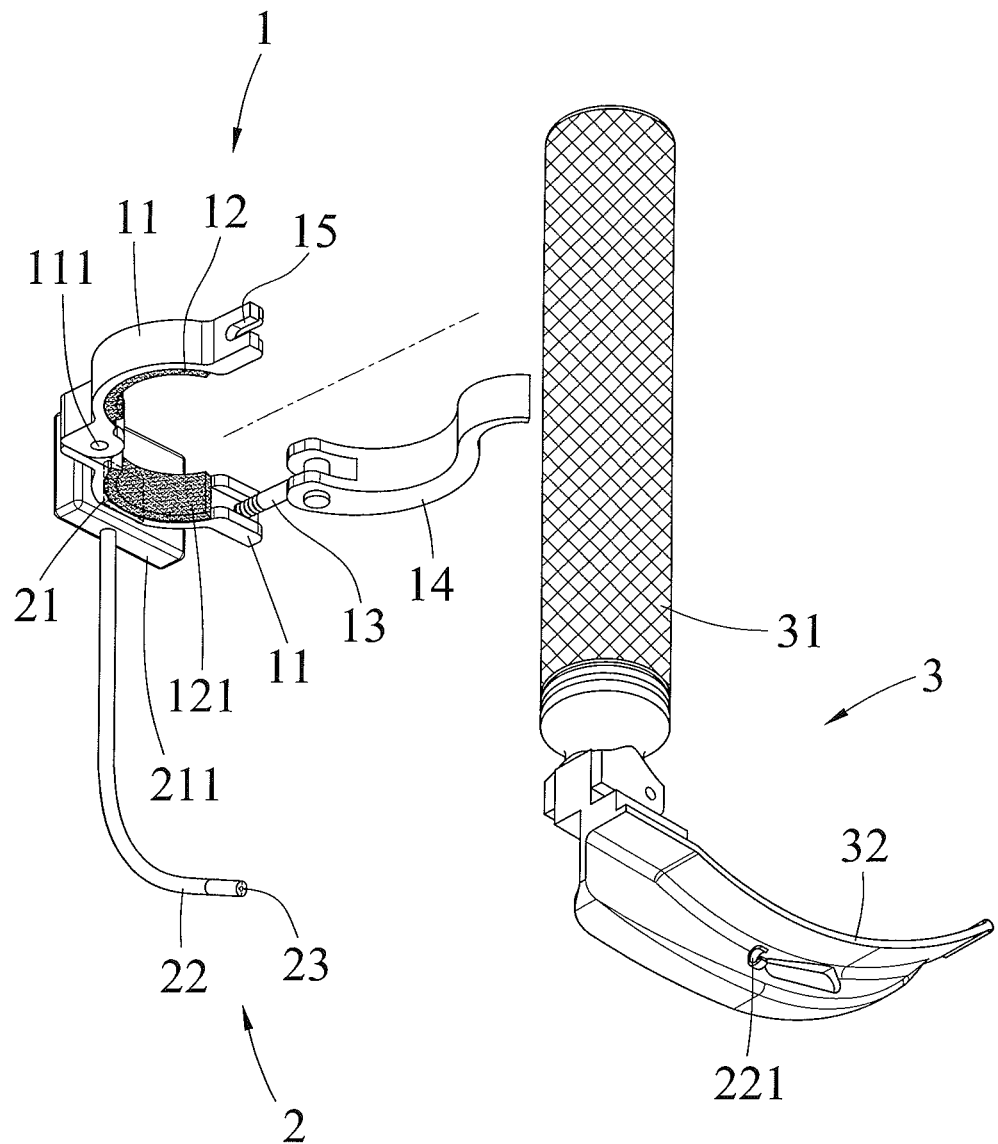
FIG. 1 is an exploded perspective view of an image type laryngoscope apparatus in accordance with the preferred embodiment of the present invention.
Figure 2:
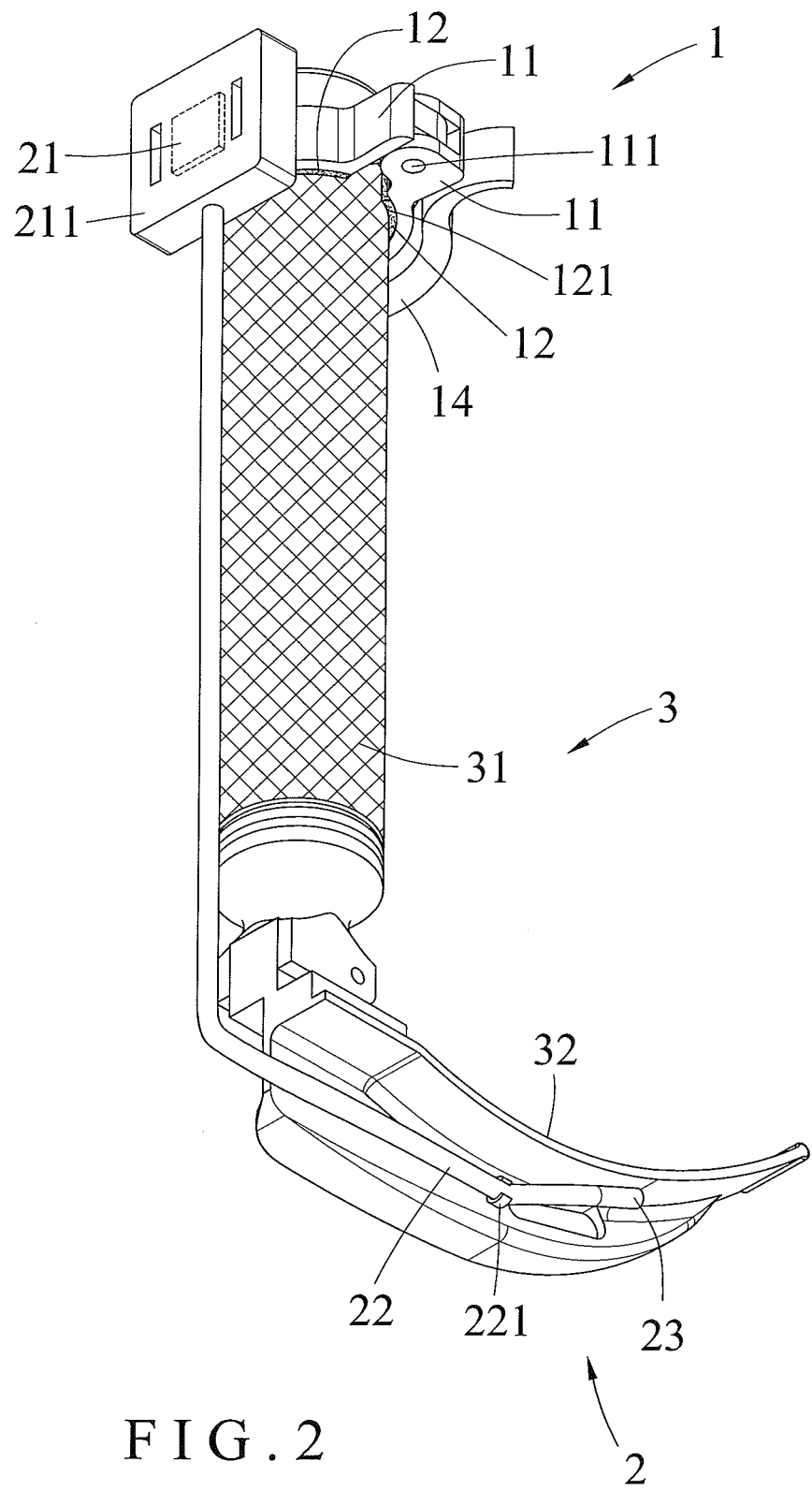
FIG. 2 is a perspective assembly view of the image type laryngoscope apparatus as shown in FIG. 1.
Figure 3:
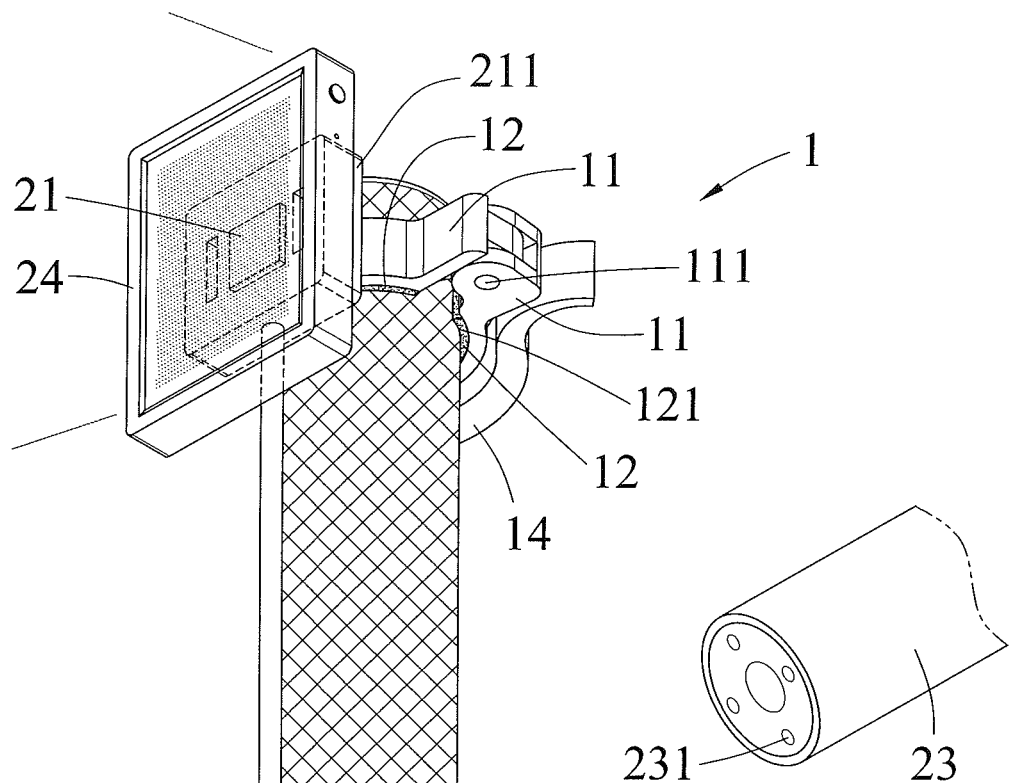
FIG. 3 is a perspective view of a laryngoscope of the image type laryngoscope apparatus as shown in FIG. 1.

Referring to the drawings and initially to FIGS. 1-5, an image type laryngoscope apparatus in accordance with the preferred embodiment of the present invention comprises a laryngoscope 3, a fastening device 1 and an image device 2.

The laryngoscope 3 includes a handle 31 and a tongue pressing plate 32 connected with a lower end of the handle 31.

The fastening device 1 includes two symmetric clamping members 11, a connecting rod 13 and a driving lever 14. Each of the clamping members 11 is provided with an arcuate groove 12 abutting the handle 31 of the laryngoscope 3 so that the handle 31 of the laryngoscope 3 has an upper end clamped between the arcuate grooves 12 of the clamping members 11. Preferably, the arcuate groove 12 of each of the clamping members 11 is provided with an antiskid pad 121. Each of the clamping members 11 has a first end and a second end. The first end of each of the clamping members 11 is provided with a pivot end 111, and the pivot ends 111 of the clamping members 11 are pivotally connected with each other. The second end of one of the clamping members 11 is provided with an elongate slot 15. The connecting rod 13 is inserted into the elongate slot 15. The connecting rod 13 has a first end pivotally connected with the second end of the other one of the clamping members 11. The driving lever 14 is pivotally connected with a second end of the connecting rod 13. Preferably, the driving lever 14 has a shape corresponding to that of each of the clamping members 11 so that the driving lever 14 can abut one of the clamping members 11.

The image device 2 includes a signal transmitting unit 21, a guide pipe 22, a camera lens 23 and a monitor 24. The signal transmitting unit 21 is mounted on one of the clamping members 11. The guide pipe 22 is connected with the signal transmitting unit 21 and has an interior containing a signal line. The guide pipe 22 is retained by a retainer 221 which is secured on the tongue pressing plate 32 of the laryngoscope 3. The camera lens 23 is mounted on a front end of the guide pipe 22 and is located at a front end of the tongue pressing plate 32 of the laryngoscope 3. The camera lens 23 has a periphery provided with a plurality of light emitting members 231 (FIG. 3) to provide a light source. The monitor 24 is connected with the signal transmitting unit 21 by a connecting unit 211 in a wire manner.

In practice, the arcuate groove 12 of each of the clamping members 11 abuts the handle 31 of the laryngoscope 3. Then, the connecting rod 13 is pivoted and inserted into the elongate slot 15. Then, the driving lever 14 is pivoted to drive the connecting rod 13 and to force the clamping members 11 to move toward each other so as to shorten the distance between the arcuate grooves 12 of the clamping members 11, so that the clamping members 11 are closely fitted onto the handle 31 of the laryngoscope 3. Thus, the handle 31 of the laryngoscope 3 is clamped between the clamping members 11 so that the image device 2 is attached to the laryngoscope 3 by the fastening device 1. At this time, the guide pipe 22 extends to the tongue pressing plate 32 and is secured on the tongue pressing plate 32 by the retainer 221, and the camera lens 23 is located at the front end of the tongue pressing plate 32.

Figure 6:
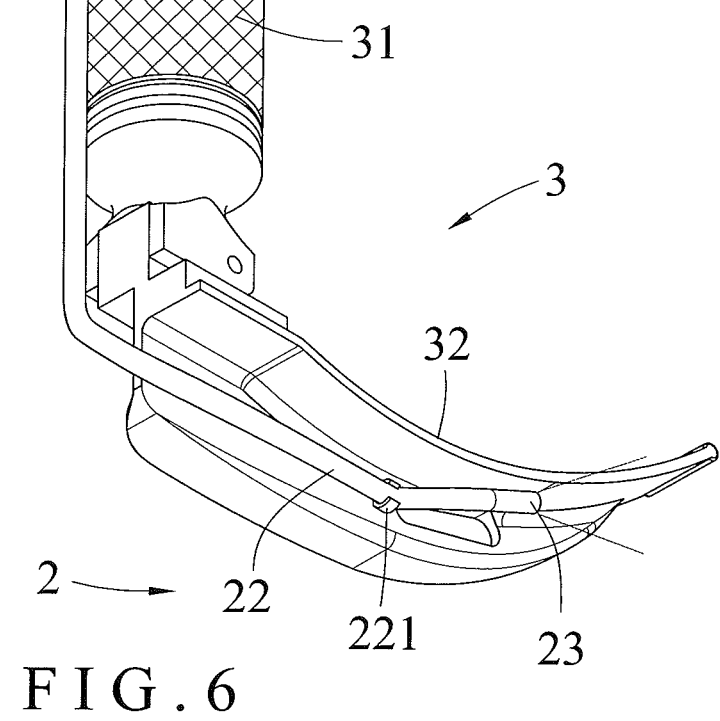
FIG. 6 is a schematic operational view of the image type laryngoscope apparatus as shown in FIG. 4 in use.
Figure 4:
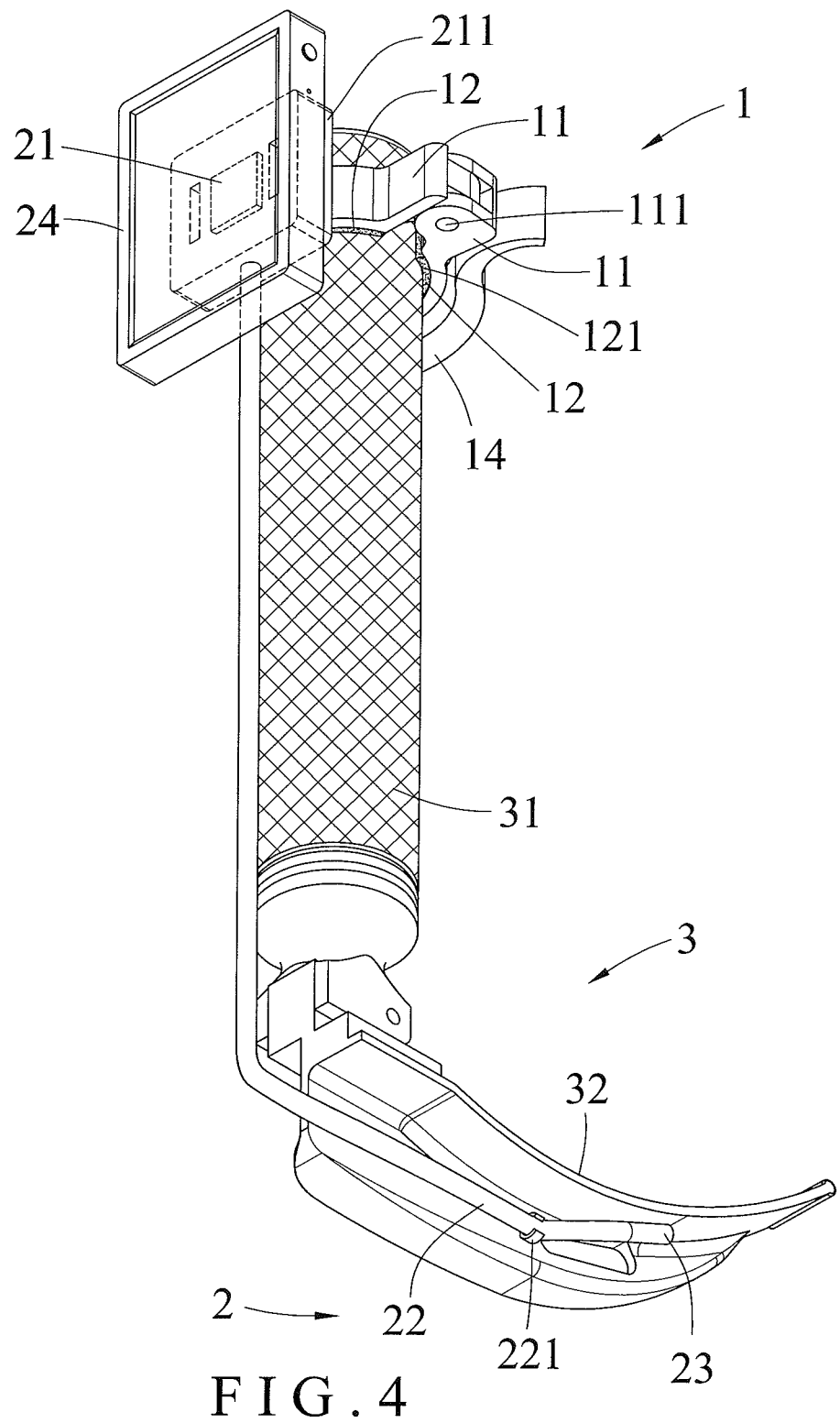
FIG. 4 is a perspective view of the image type laryngoscope apparatus for a monitor in accordance with the preferred embodiment of the present invention.
Figure 5:
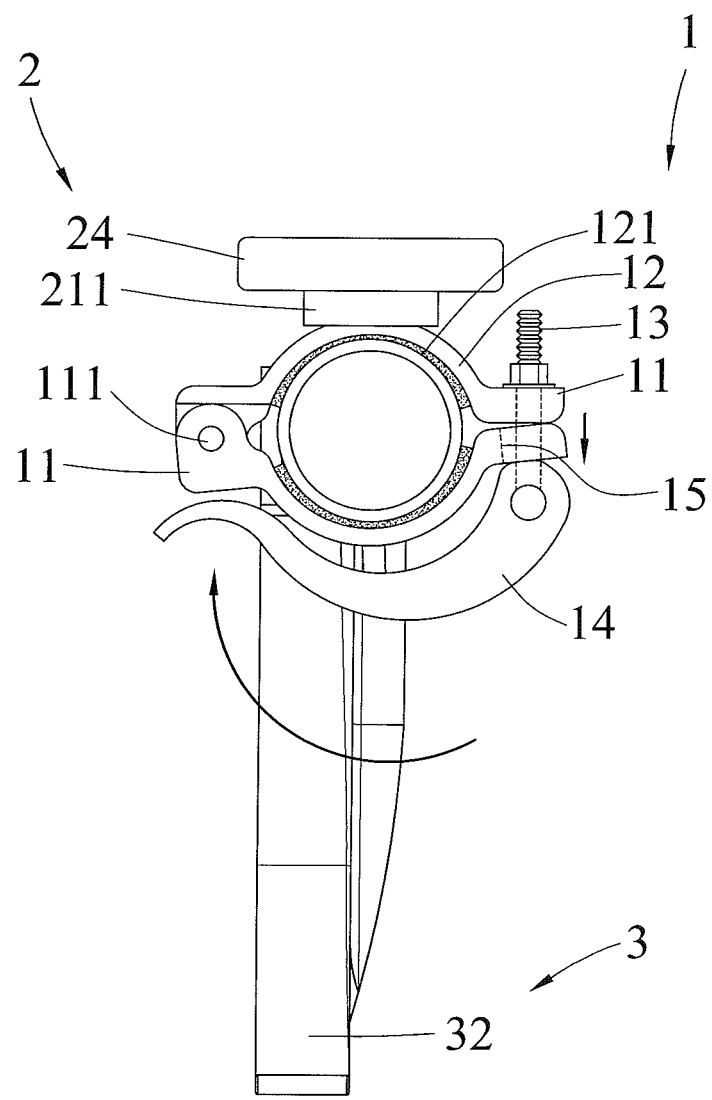
FIG. 5 is a schematic operational assembly view of the image type laryngoscope apparatus as shown in FIG. 1.

In operation, referring to FIG. 6 with reference to FIGS. 1-5, after the camera lens 23 is started, the image signals taken by the camera lens 23 are delivered to the signal transmitting unit 21 and are then transmitted to the monitor 24 in a wire transmission manner so that the operator can clearly inspect the condition of a patient's throat by the image signals.

Figure 7:
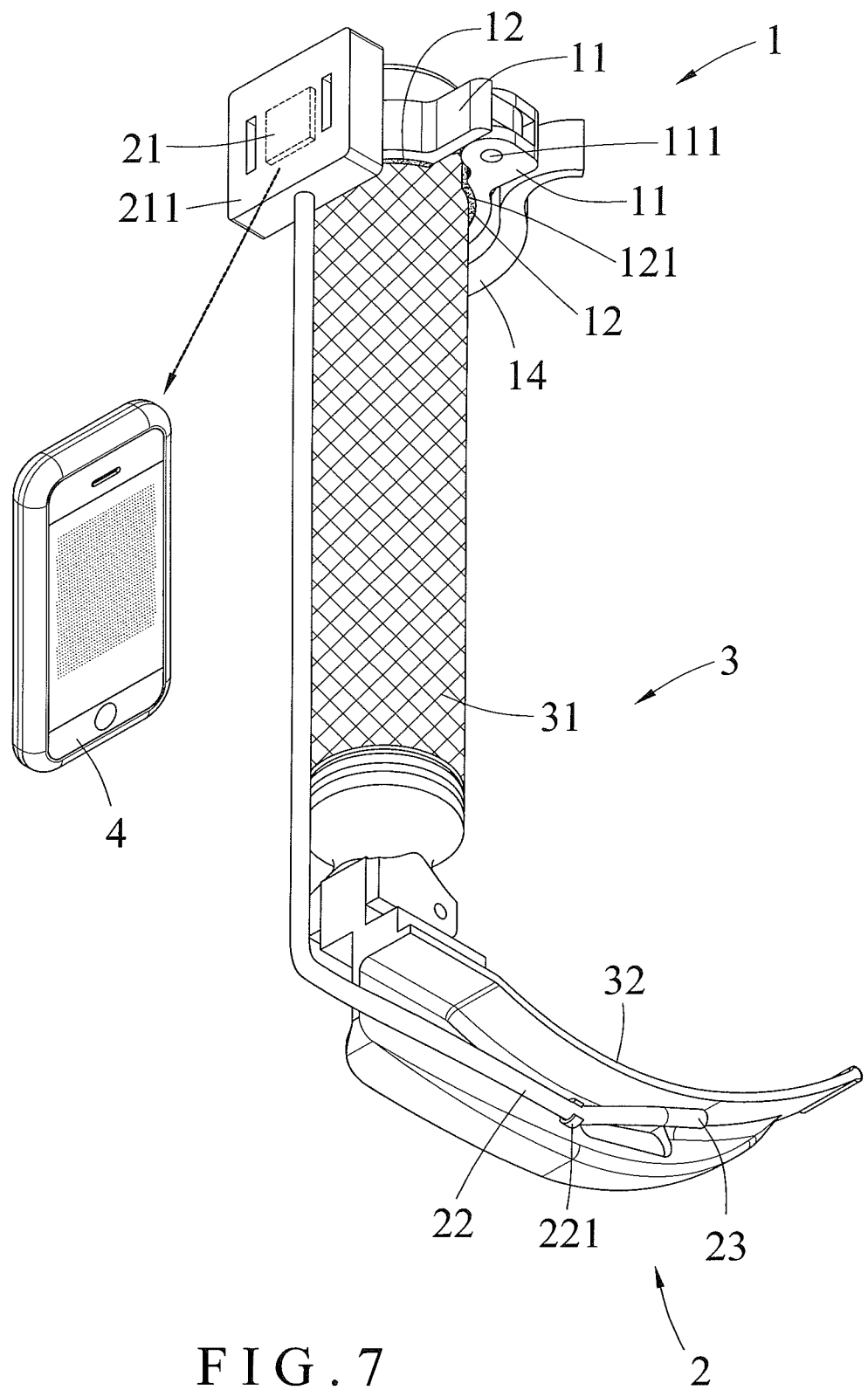
FIG. 7 is a perspective view of the image type laryngoscope apparatus for a mobile device in accordance with the preferred embodiment of the present invention.

Referring to FIG. 7, the signal transmitting unit 21 transmits the image signals to a mobile device 4 in a wireless transmission manner by bluetooth or WiFi. Preferably, the mobile device 4 is a monitor, a tablet computer or a cell phone.

Accordingly, the image device 2 is attached to the laryngoscope 3 by the fastening device 1, and the signal transmitting unit 21 transmits the image signals to the monitor 24 in a wire transmission manner or to the mobile device 4 in a wireless transmission manner, so that the operator can clearly inspect the instant condition of a patient's throat by the image signals. In addition, the image device 2 is attached to the laryngoscope 3 which has a conventional structure so that the operator can operate the laryngoscope 3 instantly without having to change his/her operational customs or habits, and without having to learn new operational methods and skills, thereby facilitating the operator operating the laryngoscope 3, and thereby saving the cost.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. An image type laryngoscope apparatus comprising: a laryngoscope, a fastening device and an image device; wherein:
   the laryngoscope includes a handle and a tongue pressing plate connected with the handle;
   the fastening device includes two clamping members, a connecting rod and a driving lever;
   each of the clamping members is provided with an arcuate groove abutting the handle of the laryngoscope;
   each of the clamping members has a first end and a second end;
   the first end of each of the clamping members is provided with a pivot end, and the pivot ends of the clamping members are pivotally connected with each other;
   the second end of one of the clamping members is provided with an elongate slot;
   the connecting rod is inserted into the elongate slot;
   the connecting rod has a first end pivotally connected with the second end of the other one of the clamping members;
   the driving lever is pivotally connected with a second end of the connecting rod;
   the image device includes a signal transmitting unit, a guide pipe, a camera lens and a monitor;
   the signal transmitting unit is mounted on one of the clamping members;
   the guide pipe is connected with the signal transmitting unit;
   the camera lens is mounted on a front end of the guide pipe and is located at a front end of the tongue pressing plate of the laryngoscope; and
   the monitor is connected with the signal transmitting unit by a connecting unit in a wire manner.

2. The image type laryngoscope apparatus of claim 1, wherein the signal transmitting unit transmits image signals to a mobile device in a wireless transmission manner by bluetooth or WiFi.

3. The image type laryngoscope apparatus of claim 2, wherein the mobile device is a monitor, a tablet computer or a cell phone.

4. The image type laryngoscope apparatus of claim 1, wherein the driving lever has a shape corresponding to that of each of the clamping members so that the driving lever can abut one of the clamping members.

5. The image type laryngoscope apparatus of claim 1, wherein the arcuate groove of each of the clamping members is provided with an antiskid pad.

6. The image type laryngoscope apparatus of claim 1, wherein the camera lens has a periphery provided with a plurality of light emitting members.

7. The image type laryngoscope apparatus of claim 1, wherein the guide pipe is retained by a retainer which is secured on the tongue pressing plate of the laryngoscope.

* * * * *